United States Patent [19]

Malhotra

[11] Patent Number: 4,497,652

[45] Date of Patent: Feb. 5, 1985

[54] DIPHENOXYMETHYLPYRIDINE HERBICIDES

[75] Inventor: Sudarshan K. Malhotra, Walnut Creek, Calif.

[73] Assignee: The Dow Chemical Company, Midland, Mich.

[21] Appl. No.: 452,585

[22] Filed: Dec. 23, 1982

[51] Int. Cl.³ ............................................ A01N 43/40
[52] U.S. Cl. .................................... 71/94; 71/DIG. 1
[58] Field of Search ............................................. 71/94

[56] References Cited

U.S. PATENT DOCUMENTS

| | | | |
|---|---|---|---|
| 3,429,689 | 2/1969 | Duerr et al. | 71/94 |
| 3,637,720 | 1/1972 | Noshiyama et al. | 71/94 |
| 3,655,359 | 4/1972 | Krumkalns et al. | 71/94 |
| 4,349,680 | 9/1982 | Malhotra | 546/302 |

*Primary Examiner*—Catherine L. Mills
*Attorney, Agent, or Firm*—S. Preston Jones; Ronald G. Brookens

[57] ABSTRACT

Disclosed are diphenoxymethyl pyridines, their preparation and their use as herbicides.

7 Claims, No Drawings

DIPHENOXYMETHYLPYRIDINE HERBICIDES

SUMMARY OF THE INVENTION

The present invention is directed to the herbicidal use of compounds corresponding to the formula

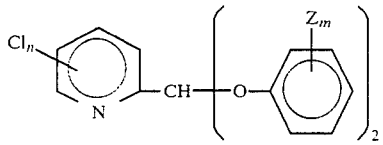

wherein n represents an integer of 1 or 2; Z represents chloro, fluoro or alkoxy of 1 to 4 carbon atoms and m represents an integer of 0, 1 or 2.

In the present specification and claims, the terms "alkoxy" and alkylthio designate straight-chain, branched-chain or cyclic alkyl groups.

The term "halo" as employed in the present specification and claims designates either bromo, chloro and fluoro.

The substituted pyridine compounds employed in the method of the present invention are either solids or liquids which are only slightly soluble in water and are usually moderately to highly soluble in common organic solvents. The substituted pyridine compounds have been found to be very effective pre- and/or post-emergent herbicides for the control of one or more plant species.

The substituted pyridine compounds employed in the method of the present invention compounds which have been found to be useful in the practice of the present invention include, amoung others for example: 6-chloro-2-(diphenoxymethyl)pyridine (Compound 1); 5-chloro-2-(diphenoxymethyl)pyridine (Compound 2); 3-chloro-2-(diphenoxymethyl)pyridine (Compound 3); 6-chloro-2-(bis(3-fluorophenoxy)methyl)pyridine (Compound 4); 6-chloro-2-(bis(4-fluorophenoxy)methyl)-pyridine (Compound 5); 6-chloro-2-(bis(4-chlorophenoxy)methyl)pyridine (Compound 6); 6-chloro-2-(bis(4-methoxyphenoxy)methylpyridine (Compound 7); 6-chloro-2-(bis(3,4-dichlorophenoxy)methyl)pyridine (Compound 8); 3,5-dichloro-2-(diphenoxymethyl)pyridine (Compound 9); and 5,6-dichloro-2-(diphenoxymethyl)-pyridine (Compound 10).

The compounds which correspond to the formula

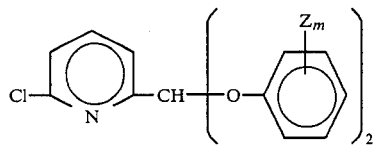

wherein Z and m are as hereinabove defined are known compounds and can be prepared as taught in U.S. Pat. Nos. 4,324,896, 4,349,680 and 4,351,943.

Those compounds which correspond to the formula

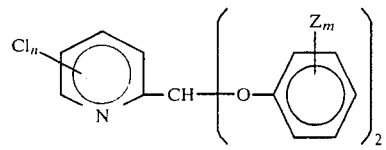

wherein n, Z and m are as hereinabove defined can be prepared by processes analogous to those taught in U.S. Pat. Nos. 4,324,896 and 4,349,680 wherein one mole of an appropriate chloro substituted-2-(dichloromethyl) pyridine is reacted with 2 moles of an appropriate phenol.

The chloro substituted-2-(dichloromethyl) pyridines employed as starting materials are known compounds and can be prepared as taught in U.S. Pat. No. 3,687,827 and U.S. Pat. No. 3,838,159.

In accordance with the present invention, it has been discovered that the diphenoxymethylpyridine compounds of the present invention are useful as pre- and post-emergent herbicides. In accordance with this invention, a method for controlling or inhibiting the growth of undesirable plant species is provided which comprises applying to plants, plant parts or their habitat, an effective or growth inhibiting or herbicidally effective amount of at least one of the compounds as set forth hereinabove.

An outstanding feature of the present invention is the ability of the presently claimed compounds to control, either by post-emergent or pre-emergent application, the growth of one or more of the grasses and broadleaf plants, such as, for example, barnyard grass, crabgrass, yellow foxtail, wild oats, pigweed, cotton, velvet leaf, morning glory and yellow nutsedge.

The application of the compounds of the present invention to plants and plant parts and their habitats, gives rise to varying degrees of response to the compounds depending upon the nature of the plant or seed, the stage of growth or maturity of the plant, the specific compound employed, and the dosage at which plant or plant part or habitat exposure to the compound is carried out, as well as environmental conditions.

The minimum amount of active compound applied should be that which is effective in controlling and/or killing undesirable plant growth. Ordinarily, for pre-emergent control, good results are obtained when from 0.06 to 4 pounds or more of at least one of the active compounds are applied per acre. In foliage treatment, good results are obtained when from 0.02 to 4 pounds of active compound per acre are employed. In selective applications to foliage for the control of many undesirable weeds in the presence of desired crop plants, a uniform dosage of from about 0.02 to 2 pounds of active compound can be employed.

The present invention can be carried out by directly employing the claimed compounds singly or in combination with each other. However, the present invention also embraces the employment of liquid, granular, encapsulated or dust compositions containing at least one of said compounds. In such usage, the compound or compounds can be modified with one or more of a plurality of chemically inert additaments or pesticidal materials including solvents or other liquid carriers, surface active dispersing agents or coarsely or finely divided inert solids. The augmented compositions are also adapted to be employed as concentrates and subsequently diluted with additional inert carrier to produce other compositions in the form of dusts, sprays, granules, washes or drenches. In compositions where the additament is a coarsely or finely divided solid, a surface active agent or the combination of a surface active agent and a liquid additament, the added material cooperates with the active component so as to facilitate the invention. Whether the composition is employed in liquid form, as a wettable powder, or as a granular encapsulated material, the active compound will normally be present in an amount of from about 5 to about 95 percent by weight of the total composition.

In the preparation of dust compositions, the toxicant products can be compounded with any of the finely divided solids, such as, for example, pyrophyllite, talc, chalk, gypsum, fuller's earth, bentonite, attapulgite, and the like. In such operations, the finely divided carrier is ground or mixed with the toxicant or wet with a solution of the toxicant in a volatile organic solvent. Also, such dust compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided clays such as, for example, attapulgite, bentonite, diatomite, or the like.

Similarly, the toxicant products can be compounded with a suitable water-immiscible organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Preferred dispersing agents which can be employed in these compositions, are oil-soluble materials including non-ionic emulsifiers such as, for example, the condensation products of alkylene oxides with the inorganic acids, polyoxyethylene derivatives or sorbitan esters, complex, ether alcohols and the like. Also, oil-soluble ionic emulsifying agents such as mahogany soaps can be used. Suitable organic liquids which can be employed in the composition include, for example, petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an organic liquid such as, for example, acetone, methylene chloride, chlorobenzene and petroleum distillates. The preferred organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point about 80° C. The proportion of the compounds of this invention employed in a suitable solvent may vary from about 2 to about 50 percent or higher.

In further embodiments, the compounds as employed in accordance with the present invention, or compositions containing the same, can be advantageously employed in the present invention in combination with one or more pesticidal or preservative compounds. In such embodiments, the pesticidal or preservative compound is employed either as a supplemental toxicant or as an additament. Representative operable pesticidal or preservative compounds include substituted phenols, cresols, substituted cresols and their metal salts, bisphenols and thiobisphenols; halogenated salicylanilides, organo sulfur compounds, carbamate compounds, quaternary ammonium compounds, organometallic compounds, inorganic salts and miscellaneous other compounds, such as phenol, cresol, trichlorophenols, tetrachlorophenols, pentachlorophenol, P-chloro-m-cresol, sodium pentachlorophenol and other sodium potassium, etc. salts of the phenols, substituted phenols, cresols and substituted cresols, di- and tribrominated salicylanilides, 2,2'-methylenebis(3,4,6-trichlorophenol), 2,2'-thiobis(4,6-dichlorophenoxide), halogenated trifluoromethyl salicylanilide, disodium ethylenebisthiocarbamate, sodium N-methyldithiocarbamate, zinc dimethyldithiocarbamate, 2-mercaptobenzothiazole, 3,5-dimethyltetrahydro-1,3,5-2H-thioadiazine-2-thione, 2,3-dinitro-1,4-dithia-anthraquinone, dodecyl pyridinium chloride, alkyl dimethylbenzylammonium chloride, dialkyl dimethylammonium chloride, bis-tributyltin oxide, bis-tripropyltin oxide, copper pentachlorophenate, copper 8-hydroxyquinolate, sodium borate, 9-undecylenic acid, 10,10'-oxybisphenoxarsine, 1-(3-chloroallyl)-3,5,7-triaza-1-azonia-adamantane chloride, 1,4-bromobisacetobutene and substituted phosphorothioates (soil applied insecticides).

In application to an area to be treated, the compounds of this invention may be applied by spraying or by the use of mechanical spreaders in accordance with conventional practice. With respect to application, however, it will be noted that, depending upon the particular circumstances encountered, one method of application may be preferably over others. Thus, for example, for preferred pre-emergence application it has been found very satisfactory to apply the active compound in a liquid spray or on granules and incorporate it into the soil.

In a further method, the distribution can be accomplished by introducing a toxicant or toxicants into the water employed to irrigate the soil. In this method, the amount of water can be varied in accordance with the moisture equivalent or field capacity of the soil in order to obtain the desired depth of distribution of the toxicant.

The following embodiments are illustrative of the present methods.

EXAMPLE I

Forty-five parts by weight of 6-chloro-2-(bis(3-chlorophenoxy)methyl)pyridine is mixed and ground with 5 parts by weight of Triton X-155 surfactant (an alkylated aryl polyether alcohol) to prepare a water-dispersible concentrate composition containing 90 percent by weight of the ester compound.

In a further operation, 25 parts by weight of 6-chloro-2-(bis(4-methoxyphenoxy)methyl)pyridine, 10 parts by weight of Triton X-155 surfactant and 65 parts by weight of xylene are mixed together to prepare an emulsifiable concentrate composition containing 25 percent by weight of said ester compound.

A mixture of 10 parts by weight of 6-chloro-2-(bis(3,4-dichlorophenoxy)methyl)pyridine, 10 parts by weight of 3,5-dichloro-2-(diphenoxymethyl)pyridine 0.1 part of Nacconol NR detergent (alkyl sulfonate), 0.1 part of Daxad No. 27 (a polymerized sodium salt of benzoid alkyl sulfonic acids) and 200 parts of water are ball-milled together to prepare a water dispersible liquid concentrate composition containing 20 parts by weight of the mixed pyridine compounds. The concentrate compositions thus prepared can be dispersed in water to prepare aqueous compositions which have very desirable wetting and penetrating properties and are adapted to distribute growth inhibiting amounts of the diphenoxymethylpyridine compounds on plant parts.

EXAMPLE II

Representative products of the present invention were evaluated for the post-emergent control of crabgrass. In these evaluations, plots of the above plant species grown to a height of about 4 inches were used. Aqueous spray compositions, each containing 4,000 parts of a given diphenoxymethyl pyridine compound per million parts of ultimate composition, were prepared by admixing a predetermined amount of the diphenoxymethyl pyridine in a predetermined amount of water-surfactant mixture to give an aqueous dispersion containing 4,000 parts of the compound per million parts of the ultimate dispersion. Each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated.

It was determined that each of Compounds 1, 3, 4, 5 and 9 gave at least 90 percent kill and control of the crabgrass plants.

EXAMPLE III

Representative products of the present invention were evaluated for the post-emergent control of pigweed. In these evaluations, plots of the above plant species grown to a height of about 4 inches were used. Aqueous spray compositions, each containing 4,000 parts of a given diphenoxymethyl pyridine compound per million parts of ultimate composition, were prepared by in accordance with Example II and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment the plots were examined for plant growth and evaluated.

It was determined that each of Compounds 1, 4, 5 and 9 gave 100 percent kill and control of pigweed plants. It was also determined that compound 10 gave at least 70 percent kill and control of the same plant specie.

In other operations carried out employing substantially the same procedures as in Examples VIII and IX, it was found that Compounds 1, 4 and 8 gave at least 80 percent kill and control of morning glory; Compounds 4 and 9 were found to give at least 90 percent kill and control of yellow foxtail; and Compounds 3 was found to give at least 80 percent kill and control of wild oats and 100 percent kill and control of barnyard grass.

EXAMPLE IV

Aqueous compositions of various compounds prepared in a manner similar to that of Example VIII were employed for pre-emergent applications on plots immediately after they were seeded with crabgrass and barnyard grass. Other plots similarly seeded with the above plant species were treated with like compositions containing no toxicant to serve as control plots. The treating applications were carried out by drenching the soil with the aqueous compositions to obtain a treating rate of 10 pounds per acre. Thereafter, the plots were maintained under conditions conducive for good plant growth. Two weeks after treatment, the plots were examined to determine the percent plant growth and evaluated.

It was determined that each of Compounds 1, 2, 3, 4, 5, 7, 8 and 9 gave at least 85 percent kill and control of crabgrass and barnyard grass.

In other operations carried out employing substantially the same procedures as in Example X, it was found that compounds 1, 4 and 5 gave 100 percent kill and control of morning glory and Compounds 1, 2, 4 and 5 gave 100 percent kill and control of pigweeds.

EXAMPLE V

Aqueous compositions of various compounds prepared in a manner similar to that of Example II were employed for a pre-emergent applications on plots immediately after their being seeded with seeds of yellow foxtail and wild oats. Other plots similarly to be seeded with the above plant specie were treated with the like compositions containing no toxicant to serve as control plots. The treating applications were carried out by drenching the soil with the aqueous compositions to a depth of about one inch to obtain a treating rate of 10 pounds per acre. Thereafter, the plots were maintained under conditions conducive for good plant growth. Two weeks after treatment, the plots were examined to determine the percent plant growth and evaluated. It was found that Compounds 1, 3, 4, 5, 6, 7, 8 and 9 gave substantially 100 percent kill and control of yellow foxtail; and Compounds 1, 3, 4, 5, 8 and 9 gave at least 90 percent kill and control of wild oats.

What is claimed is:

1. A method for controlling the growth of undesirable plants which comprises applying to plants, plant parts or their habitat a composition which comprises an inert carrier in admixture with a herbicidally effective amount of a compound corresponding to the formula

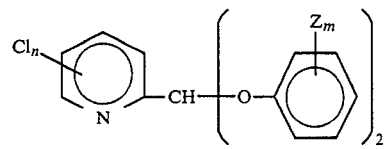

wherein n represents an integer of 1 or 2; Z represents chloro, fluoro, or alkoxy of 1 to 4 carbon atoms and m represents an integer of 0, 1 or 2.

2. The method as defined in claim 1 wherein the compound is 6-chloro-2-(diphenoxymethyl)pryidine.

3. The method as defined in claim 1 wherein the compound is 5-chloro-2-(diphenoxymethyl)pryidine.

4. The method as defined in claim 1 wherein the compound is 3-chloro-2-(diphenoxymethyl)pyridine.

5. The method as defined in claim 1 wherein the compound is 6-chloro-2-(bis(3-fluorophenoxy)methyl)pyridine.

6. The method as defined in claim 1 wherein the compound is 6-chloro-2-(bis(4-fluorophenoxy)methyl)pyridine.

7. The method as defined in claim 1 wherein the compound is b 3,5-dichloro-2-(diphenoxymethyl)pyridine.

* * * * *